July 14, 1953 J. VALDERO Plant Pat. 1,205
PEACH TREE
Filed Oct. 30, 1951
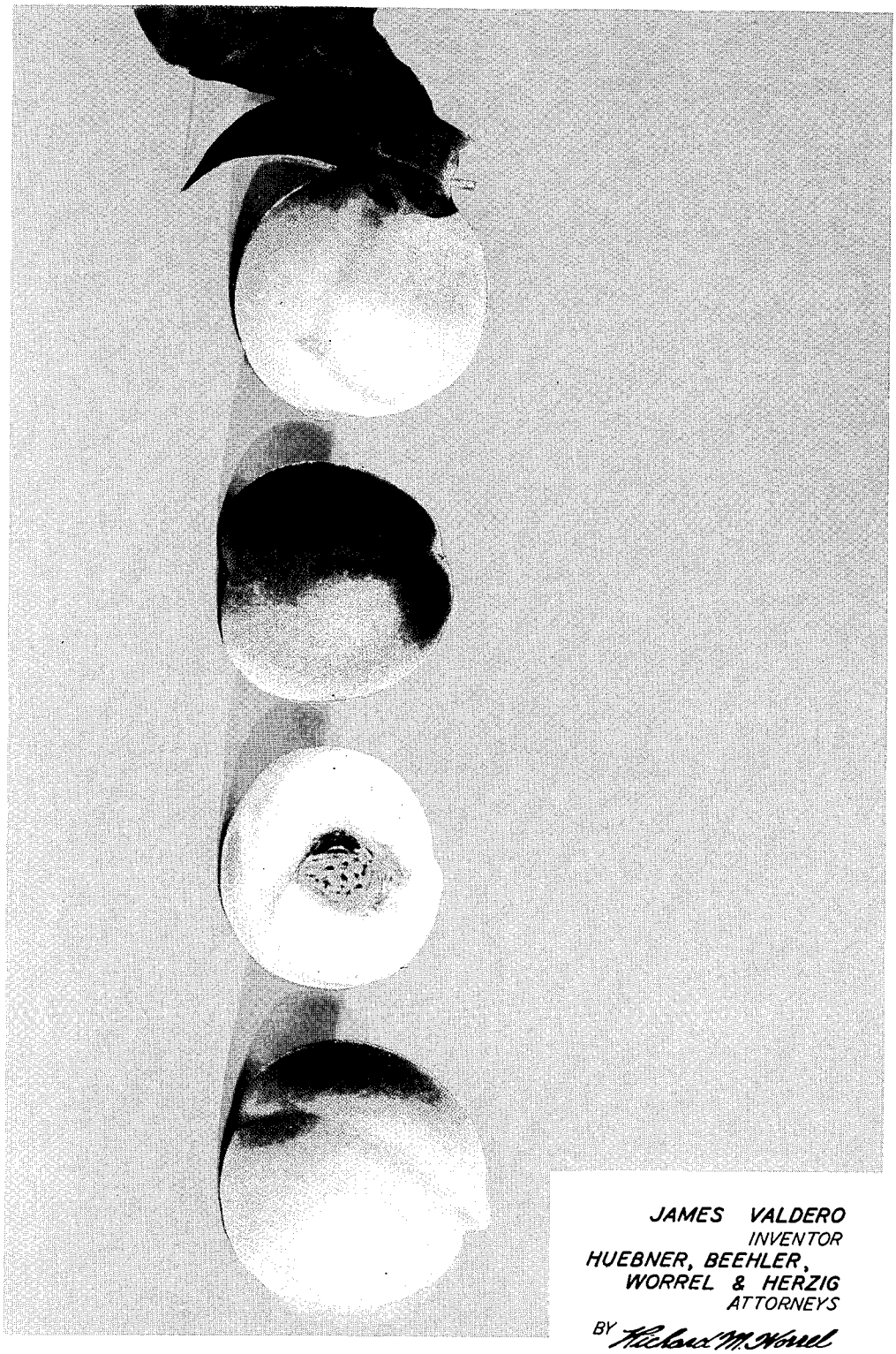
JAMES VALDERO
INVENTOR
HUEBNER, BEEHLER,
WORREL & HERZIG
ATTORNEYS
BY Richard M. Worrel Patented July 14, 1953

Plant Pat. 1,205

UNITED STATES PATENT OFFICE 1,205

PEACH TREE

James Valdero, Parlier, Calif.

Application October 30, 1951, Serial No. 253,768

1 Claim. (Cl. 47—62)

The present invention relates to a new and distinctive variety of peach tree having freestone fruit of somewhat general similarity to the well-known Babcock variety but differing therefrom in certain significant characteristics.

The subject peach tree originated as a chance seedling in the sense that it did not result from the artificial cross pollination of selected parent peach trees by the applicant but is an intentionally produced new variety inasmuch as it resulted from the purposeful germination of one of numerous seeds selected by the applicant and the care of the resultant seedlings until they bore fruit enabling discriminating selection for reproduction. The applicant is a peach farmer who usually dries his commercial peach crop for market. Preliminary to the drying operation, the peaches are cut into substantially equal halves for exposure to the sun and the pits removed therefrom in the well-known manner. Vast quantities of pits result as a by-product of each year's drying operation. The applicant, at the end of the drying seasons, frequently selects pits from the seasonal accumulation thereof which he germinates and cares for until the characteristics of the resultant seedlings can be determined. The seedlings which have no particular attributes are budded or grafted over to known varieties for orchard replacement purposes and those of noteworthy characteristics are kept for further observation and reproduction, if of sufficient significance to warrant the care and attention required. The present peach tree resulted from a pit selected by the applicant, which he germinated with numerous other pits selected at the same time, and which he discovered to possess noteworthy characteristics while growing with its companion seedlings in his orchard near the city of Sanger, county of Fresno, in the San Joaquin Valley of the State of California.

Inasmuch as the pit which resulted in the subject tree was selected from a season's accumulation of pits, its parentage is not known. Judging from its unusual attributes, however, which the applicant recognized and preserved by asexual reproduction, it is believed to be a chance cross between an unnamed seedling peach tree developed earlier by the applicant, but for which no patent protection has ever been requested, having somewhat larger, pale skinned white fleshed, freestone fruit and the Rio Oso Gem of Plant Patent No. 84 to Yerkes.

The applicant has reproduced numerous other trees of the subject variety on his farm near Sanger, California, to which reference has been made, until he now has an orchard of the new variety several acres in extent and sufficient to justify commercial packing and shipping of the fruit. Reproduction has been accomplished by budding scions of the subject variety on various root stocks. Inasmuch as the characteristics of peach trees and the fruit borne thereby are known to vary according to soil, climate and cultural distinctions, the characteristics of the subject peach tree described herein are those resulting from the oecologic conditions prevailing at the applicant's ranch. The resultant trees have flourished and consistently maintained the characteristics described herein establishing the dependability thereof.

For illustrative purposes, several characteristic fruit, a small twig, and several leaves are shown in the accompanying photographic print which has been tinted to impart as true coloring thereto as the representing medium permits.

In the dormant stage there is no particular distinguishing characteristic that has been noted. The trees are medium large, open headed, broad topped and usually without a central leader. The trunk of the tree at maturity is medium stocky and usually from nine inches to a foot in diameter and of the usual dark reddish brown color. As is usual in peach trees, the trunk is usually smooth until it reaches a diameter of from one and a half to two inches, after which it becomes rough and scaly. The branches are generally more upwardly directed than the outwardly extended branches of the Rio Oso Gem, of average vigor and size, and subject to some drooping when heavily ladened, as are peach branches generally. The twigs are round, rather slender, and glabrous. They are grassy green when small and change to reddish brown with age.

The tree blossoms early, preceding by about one week in the area of present cultivation, the well known Elbertas, J. H. Hales, Nectars, and Lovels, believed to be unpatented varieties and the Rio Oso Gem of Plant Patent No. 84. The buds are medium large and the blossoms large and attractive, being a bright pink very similar to blossoms of the unpatented Mayflower variety which blooms several weeks later. The blossoms have five petals of generally ovate form and five calyx lobes. During the blooming period the tree is readily distinguished from all other peach trees of general cultivation in the San Joaquin Valley by its ornamental appearance incident to the rich pink Mayflower coloring of its blossoms not known in other peach trees of similar blooming period. The blossoms are appreciably darker than the blossoms of the Rio Oso Gem.

During the growing season, the most impressive distinguishing feature of the subject peach tree when viewed from a distance is the intensely bright green color of the leaves, approximating Leek Green, Plate 000858 Chart II, page 197 of Robert F. Wilson's Horticultural Charts. The upper surfaces of the leaves are slightly brighter than the lower surfaces thereof. No other peach tree known to the applicant has leaves approaching the subject variety in brilliance. The leaves are medium broad, of alternate occurrence, symmetrical, lanceolate, and have marked midribs with frequently alternately branching, occasionally concurrently branching, side ribs. The leaves usually have long tapering apices, parabolic bases, are approximately 1¾ inches in width and 6¼ inches in length at maturity and have minutely serrated edges. The petioles are stout, longitudinally grooved along the upper surfaces and usually have a pair of glands at leaf base. The intensely bright green coloring of the leaves prevails until frost without any perceptible autumnal coloring whatsoever. While leaves of companion trees of other varieties in the orchard turn yellow and red in the autumn, the leaves of the subject peach maintain their bright green coloration and after the advent of cool weather suddenly all fall to the ground.

The fruit is unlike any known to the applicant in coloring, taste and fragrance. It ripens early and is characterized by an ability to hang on the tree for a protracted period without substantial deterioration. Usually ripening about the second week in June, approximately with the Babcock, two weeks later than the Mayflower, and four weeks earlier than the regular Elberta, it is not uncommon for the fruit to remain in good condition on the tree until the latter part of July. The fruit shown in the drawing were picked July 18, 1951, and were firm and in good condition. The coloring of the drawing was double checked with fruit picked July 27, 1951, which were also firm and in good condition. For shipping purposes, however, the fruit is preferably harvested somewhat earlier.

The coloring of the subject peach as well as its acquisition of sugar occurs much earlier than other peaches having the approximate ripening period. As early as April 20, for example, fruit of the applicant's peach was already colored an attractive pink over all areas exposed to the sun and of well rounded form. The fruit on adjacent trees of Rio Oso Gems had almost no preceptible color and Nectar peaches also growing nearby possessed only very slight color. At this date the applicant's peach was more globular than either the Nectar or Rio Oso Gem which had pointed and pinched appearances. When only partially mature, the fruit is sweet, has a distinctly pear flavor and is as firm as a firm apple. The pear flavor persists until the fruit is almost completely ripened when the flavor approaches more closely that of the well known White Heath clingstone which ripens in September. Many people prefer the flavor of the applicant's peach before it reaches full maturity and while still crunchy to chew. Its early coloring and sugaring is a distinct advantage to early harvest and shipment in durable condition.

At full maturity, the flavor is more intense than that of the White Heath and many individuals who have tasted the fruit comment on a pleasantly noticeable nectarine tang blended with the White Heath flavor. Although the taste is entirely different from that of an apricot, the aroma when fully right, is definitely that of an apricot. Although taste definition is at best inaccurate, almost all who taste the subject peach, when firm, comment on the flavor similarity to a pear and when fully ripe to the blend of White Heath and nectarine flavors. The sugar content is much higher than the Elberta or J. H. Hale.

The flesh is of low acid content and resists browning to a marked extent when exposed to the air. The total acidity (as malic acid) is approximately one hour at an environmental temperature of about 95° F. before being photographed. When cut with a sharp knife and not bruised, it is possible to expose the flesh to the atmosphere for even several days without appreciable browning while the flesh is dehydrated to the condition of a commercial dried peach.

At maturity the fruit is globular, moderately to heavily pubescent, has a moderately marked suture, usually bulges slightly more at one side of the suture than the other, and is minutely mucronate. Under cultivation, the size usually approximates 2½ inches in transverse diameter and 2⅝ inches in longitudinal diameter. The tree tends to bear an excessively heavy crop and the fruit attains satisfactory size only when heavy thinning is practiced.

Where shielded from the sun, the fruit is light cream or chrome, such as Plate 10L11 of Maerz & Paul's Dictionary of Color. Where fully exposed to the sun, a dark red blush is assumed similar to Ox-Blood Red, Plate I, of Ridgway's Color Standard which in some instances is deepened by an appreciable purple quality. With partial sun exposure the fruit coloring varies through the wide range from the light chrome to the described red. The skin is adherent to the flesh until overly ripe.

The flesh varies slightly from almost pure white to light cream, about 9D2, page 41 of Maerz & Paul's Dictionary of Color and is firm and of excellent quality. The pit well is deep and varies from ox-blood red to carmine. Radial rays of carmine extend outwardly from the pit well into the flesh and are brilliantly contrasted with the light color thereof.

The stone is about 1⅛ inches in length, three-quarters of an inch in major transerve dimension and ⅝ inch in minor transverse dimension. It is usually ovate, deeply sculptured, substantially symmetrical, and has a sharp point. A sharp blade is frequently noted at the stem end thereof longitudinally extending along the dorsal side. The pit varies in color from a brilliant carmine to a dull brown dependng upon the degree of maturity.

In actual tests, the fruit has been found to ship well. Its firm flesh, early coloring, and early sugaring are conducive to excellent resistance to picking, handling, packing, and shipping damage. This is in marked contrast to the Babcock, the fruit of which is rarely shipped out of California because of the high water content and delicate nature of its flesh.

From the foregoing, it will be apparent that the subject peach tree is characterized by the following:

1. Brilliant green foliage infrequently forming autumn colors. As the leaves drop in the fall from one-half to three-fourths of the leaves are a uniformly brilliant green. The remainder of the leaves occasionally acquire a light streak of maroon or red coloring. The leaves never acquire the yellow coloration in the fall of peach trees generally.

2. Freestone fruit of firm light cream flesh, brilliant carmine pit well radiantly streaked into the flesh, and dark ox-blood red skin where exposed to the sun graduated to light cream where completely shielded from sun.

3. Ripening with Babcock but blooming earlier with bright pink appearance of Mayflower.

4. Early high sugar content, coloring, and globular form of fruit.

5. Ability of fruit to remain on tree several weeks after ripening without deterioration.

6. Fruit at early maturity of pronounced pear flavor further ripening into high sugar content, low acid, mature fruit of a flavor suggestive of White Heath clingstones with nectarine tang and observable apricot aroma.

It is to be understood that the described characteristics are typical of the applicant's peach tree under the environment of the San Joaquin Valley of California but that minor deviations and variations are to be expected under different oecological conditions.

Having described my new and improved peach tree, what I claim is:

The variety of peach tree herein illustrated and described characterized as to novelty by the brilliant green of its foliage, the firm light cream flesh of its freestone fruit having a brilliantly carmine pit well radiantly streaked into the flesh ripening approximately concurrently with the Babcock, the graduated coloring of the skin from light cream to ox-blood red, dependent upon exposure to the sun during maturation, the progressive flavor change from a pear-like quality in early maturity to that suggestive of a White Heath clingstone with a nectarine tang at full maturity, and the ability to sustain marketable condition for a protracted period when left on the tree.

JAMES VALDERO.

No references cited.